United States Patent [19]

Dong et al.

[11] Patent Number: 4,678,639

[45] Date of Patent: Jul. 7, 1987

[54] APPARATUS FOR PERIODICALLY MONITORING THE COMPOSITION OF A PLURALITY OF SAMPLES

[75] Inventors: Michael W. Dong, Norwalk; Stanley K. Yarbro, Newtown; Frank Vandermark, Shelton, all of Conn.

[73] Assignee: The Perkin-Elmer Corporation, Norwalk, Conn.

[21] Appl. No.: 585,797

[22] Filed: Mar. 2, 1984

[51] Int. Cl.$^4$ ............... G01N 21/05; G01N 33/15; G01N 35/08

[52] U.S. Cl. ................................ 422/81; 422/68; 436/52

[58] Field of Search ............... 422/63, 67, 68, 81, 422/102; 436/52; 73/432 R, 864.11, 864.22, 864.34, 863.01, 863.83; 356/410, 411

[56] References Cited

U.S. PATENT DOCUMENTS

| | | | |
|---|---|---|---|
| 2,851,655 | 9/1958 | Haddad | 422/81 |
| 3,192,774 | 7/1965 | Simoons | 73/53 |
| 3,536,450 | 10/1970 | Dus et al. | 422/81 |
| 3,802,272 | 4/1977 | Bischoff et al. | 366/142 |
| 3,881,872 | 5/1975 | Naono | 422/81 |
| 3,912,452 | 10/1975 | Sodickson et al. | 422/81 |
| 4,037,475 | 7/1977 | Topham | 73/863.01 |
| 4,108,602 | 8/1978 | Hanson et al. | 436/52 |
| 4,230,665 | 10/1980 | Huber | 422/116 |
| 4,335,438 | 6/1982 | Smolen | 422/81 |

FOREIGN PATENT DOCUMENTS 2030963  4/1980  United Kingdom ............ 73/863.83

OTHER PUBLICATIONS

Snyder et al., eds., *Intro. to Modern Liq. Chrom.*, 2nd ed., John Wiley & Sons, Inc. (N.Y.) 1979, pp. 301–304.

*Primary Examiner*—Michael S. Marcus
*Assistant Examiner*—C. M. Delahunty
*Attorney, Agent, or Firm*—Ronald G. Cummings; Francis L. Masselle; Edwin T. Grimes

[57] ABSTRACT

An apparatus for periodically monitoring the composition of a plurality of samples includes a plurality of stationary flow-through sample vials through which sample fluid is periodically passed. A sampling probe withdraws fluid from the vial for subsequent analysis.

3 Claims, 3 Drawing Figures

APPARATUS FOR PERIODICALLY MONITORING THE COMPOSITION OF A PLURALITY OF SAMPLES

BACKGROUND OF THE INVENTION

The present invention generally relates to an apparatus for periodically monitoring the composition of a plurality of samples and, in particular, relates to such an apparatus having stationary sample vials and means for selectively withdrawing sample fluid from the stationary vials.

One of the most demanding aspects of many processes, especially manufacturing processes is the need to accurately determine the composition of a fluid, or a group of fluids, at any given time. Such information is demanded not only in instances where the maintenance of a constant composition is critical, but also in instances where the change, with respect to time for example, of the composition is critical as well. Some of the better known of these latter processes is dissolution analysis of pharmaceuticals; fermentation studies; waste product elements analysis; (such as from sewage treatment plants); and environmental studies.

The dissolution analysis of pharmaceuticals is particularly important not only to protect the general public but also to comply with government regulations. This analysis is performed to ensure proper dosage uniformity. In recent times such an analysis has increased in importance and complexity due to the continuing development of multi-active ingredient medicines as well as the increased use of "time-released" medicines.

Presently, the apparatus required for such dissolution analysis studies is expensive, requires excessive volumes of samples due to the loss of sample during analysis and is frequently inaccurate due to cross-contamination of samples.

The conventional apparatus is expensive because of the required fluid conduit systems necessary to supply sequential samples to a translating sample container used during analyses. Presently, most such analyses are carried out using ultraviolet or fluoresence spectrophotometry. This requires a rather complex sample delivery system and is amenable only to single component analysis.

Further, since the sample solution, for example, one in which a tablet is dissolving, is continually reduced the results do not represent the true time dissolution in a specific volume. Hence, the measured dosage dissolved is, in fact, inaccurate.

Finally, because of the rather complex pumping and valving system required, cross-contamination between samples is a frequent occurence. Such cross-contamination results in inaccuracies in the characterizing of samples. This is a particularly acute problem for a multi-active ingredient medication.

SUMMARY OF THE INVENTION

Accordingly, one object of the present invention is to provide an apparatus for periodically monitoring the composition of a plurality of samples which avoids the above-recited difficulties.

This object is accomplished, at least in part, by an apparatus having stationary sample vials and means for selectively withdrawing sample fluid therefrom.

Other objects and advantages will become apparent to those skilled in the art from the following detailed description read in conjunction with the appended claims and the attached drawings.

BRIEF DESCRIPTION OF THE DRAWINGS

The drawings, not drawn to scale, include.

DETAILED DESCRIPTION OF THE INVENTION

Figure 1:
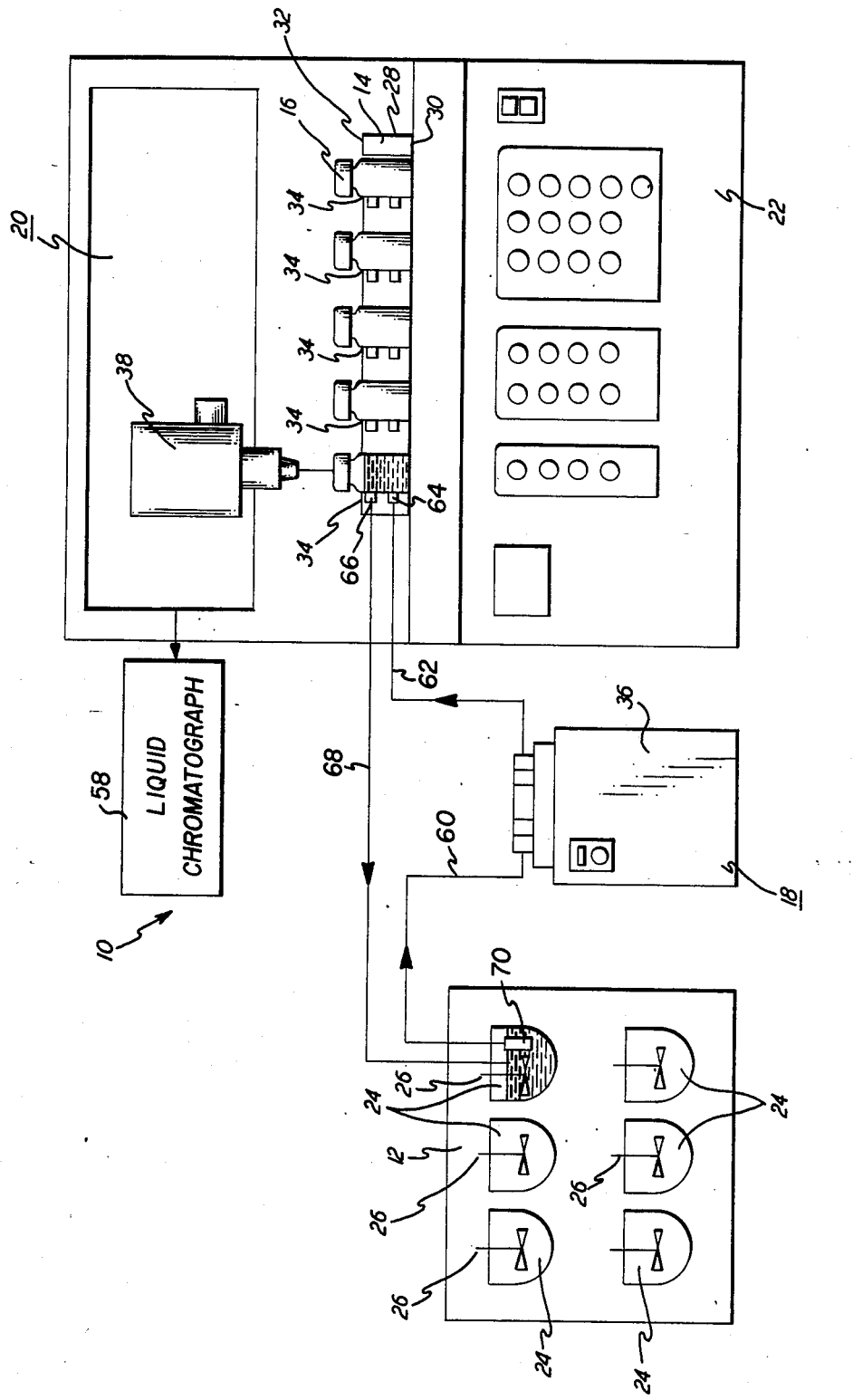
FIG. 1 which is a pictorial view of an apparatus embodying the principles of the present invention,
FIG. 2 which is a cross-sectional view of a novel flow-through sample vial useful in the apparatus of FIG. 1.
Figure 3:
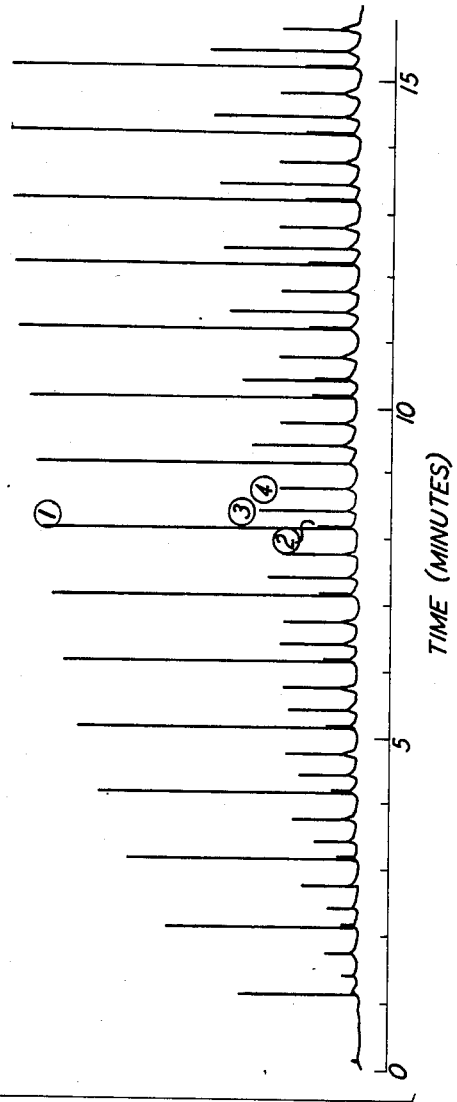
FIG. 3 is a chromatogram of a typical analysis performed by the apparatus of FIG. 1.

An apparatus for periodically monitoring the composition of a plurality of samples, generally indicated as 10 in FIG. 1 and embodying the principles of the present invention, includes a source 12 of a plurality of samples, a means 14 for accomodating at least one stationary sample vial 16, means 18 for conveying a sample from the source 12 to a sample vial 16 which vial 16 is stationary, means 20 for selectively withdrawing sample fluid from a selected stationary sample vial 16 and means 22 for controlling the sample fluid conveying means 18 and the withdrawing means 20 so that the withdrawing means 20 withdraws sample from a stationary sample vial 16 containing a flowing sample fluid.

In the preferred embodiment, the source 12 of a plurality of samples includes a plurality of sample holders 24 each such sample holder 24 having a stirrer 26, or mixer, associated therewith. Alternatively, the source 12 can be a flowing stream of fluid from which samples can be periodically removed.

The means 14 for accomodating at least one flow-through sample vial 16 can be any sample vial holder mechanism known in the art. However, in the preferred embodiment, where a plurality of stationary sample vials 16 are employed, i.e. one vial 16 to correspond to each sample holder 24, a rack 28 having a base 30 and a vial guide member 32 supported above the base 30 can be employed. In such a rack 28, the sample vials 16 are inserted through openings 34 in the guide member 32 and rest on the base 30. The rack 28 can be stationarily secured by any such means known in the art.

In the preferred embodiment, the conveying means 18 includes a multi-channel pumping mechanism 36. The multi-channel pumping mechanism 36 is best implemented by means of a plurality of peristaltic pumps, which pumps are relatively small and inexpensive. In such an arrangement a large number of different samples can be conveyed from sample holders 24 to stationary sample vials 16 without any danger of cross-contamination.

The means 20 for withdrawing sample fluid from each stationary sample vial 16 includes a translatable sampling probe 38. The position of the probe 38 is controlled by the means 22. Preferably, the means 22 is a programable dedicated data station or another computer controlled device. As aforestated, the means 22 controls both the conveying means 18 and the withdrawing means 20 preferably in a manner whereby the withdrawing means 20 is activated only when said conveying means 18 is causing fluid to flow through said sample vial.

In the preferred application the sampling probe 38 is an injection needle which withdraws a relatively small sample fluid from a vial 16 and delivers it to a liquid chromatograph apparatus 58 via which separation and subsequent analysis of the particular sample is performed.

In order to implement the apparatus 10 the stationary sample vial 16 must be a flow-through vial 16. That is, sample fluid delivered thereto via the conveying means 18 must be returned to the respective sampleholder 24. But for the flow-through excessive amounts of sample would be lost. Hence, the periodic monitoring would be inaccurate. Further, the stationary flow-through sample vial must be accessible to the sampling probe 38.

Figure 2:
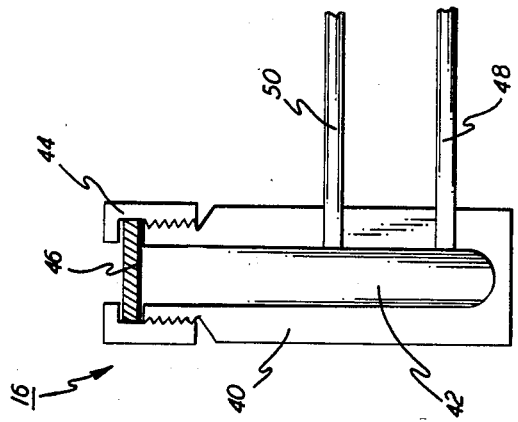

To meet these requirements a unique and novel flow-through vial 16 has been developed to provide the desired features required for the periodic monitoring of dissolving samples. One embodiment of such a vial 16 is shown in FIG. 2. Therein is shown a vial body 40 formed from polyethylene, for example, or some equally relatively inert substance. In one embodiment, the body 40 defines a sample volume cavity 42 therein. The cavity 42, in one embodiment, has a diameter of about 6 mm. The body 40 is provided with a cap 44 which retains a (polytetrofluorethylene) PTFE septum 46 thereacross which septum 46 seals the cavity 42 not only against fluid leakage but also from contamination. The body 40 is also provided with an inlet conduit 48 and an outlet conduit 50. In one particular embodiment, the conduits 48 and 50, are stainless steel tubes having gold plating on at least the inside thereof, which gold plating acts to make the stainless steel relatively inert to the particular samples being tested. Preferably, the stainless steel conduits 48 and 50, have a 1/16 inch outside diameter and a 0.043 inch inside diameter. The stainless steel conduits 48 and 50, are secured to the body by threads and epoxyed in place.

As an alternative a flow-through sample vial 16 can also be formed from a relatively inert glass during the formation of which external input and output connections can also be formed. Alternatively, such a vial 16 can be formed by injection molding techniques using commonly known plastics.

In one particular application of the apparatus 10, the number of stationary flow-through vials 16 is equal to the number of sample holders 24 which is also equal to the number of peristaltic pumps. Each sample holder includes an outlet conduit 60 extending from the holder to the input side of the particular pump dedicated thereto. The output of that pump conveys the fluid via a conduit 62 to the inlet tube 64 of the particular flow-through stationary sample vessel. The output 66 from the flow-through stationary sample vessel is connected back to that same sample holder via a return conduit 68. Preferably, the conduit 60 exiting the sample holder 24 includes a filter 70 attached thereto, whereby any particulate matter such as from a partially dissolved medication tablet is prevented from flowing in the conduit and remains in the sample fluid to continue dissolution. The control means is preferably a model LCI-100 which is a Laboratory Computing Integrator marketed by The Perkin-Elmer Corporation, Norwalk, Conn. and the withdrawing means is an ISS-100 which is an Intelligent Sampling System also marketed by The Perkin-Elmer Corporation, Norwalk, Conn.

In one particular analysis, which demonstrates the relatively inexpensive flexible and accurate nature of the present apparatus, one analgesic tablet was placed in a bath of 900 mm. of 0.1N of hydrochloric acid. The sample was pumped through a stationary sample vial at the rate of $2\frac{1}{2}$ ml. per minute and was sampled at one injection per minute.

In order to take maximum advantage of the available analytical techniques a short liquid chromatography separating column was used having a bed of carbon 18 bonded silica support. The mobile phase was 18 percent $CH_3CN$ in 1 percent $H_3PO_4$. The operating conditions were 3.5 ml. per minute, flow rate at a pressure of 2800 lbs. per square inch, using an ultra violet detector at 240 manometers. Such operating conditions require only a 10 microliter volume injection and clearly due to the flow through feature of a sealed vial the sample loss is negligible. As shown therein, the four major components of the tablet were sampled and monitored at 1 minute intervals. It can be seen that the tablet was fully dissolved after about 13 to 15 minutes. If the same test where to be performed under the same conditions and apparatus available to the pharmaceutical industry such an analysis would require on the order of about 5–10 hours.

In an actual analysis one of the sample holders 24, or more conveniently a vial which may or may not be a flow-through type, will contain a standard solution to provide a baseline measurement. Such a baseline measurement is desirable in order to monitor other elements of the analytical system, such as a separating column.

From the above discussion, it will be understood that the apparatus described herein is not only relatively inexpensive, single to operate, in fact it can be fully automated by use of a data station controlled by known microprocessors. The apparatus is also extremely accurate and avoids cross-contamination between a plurality of sample fluids. This advantage is derived from the fact that each sample holder has a single stationary sample vial associated therewith and both sample input conduits and sample output conduits associate therewith.

In a particular application in the pharmaceutical industry it will be understood that more than a single tablet or medication under examination would be simultaneously analyzed. Although FIG. 1 indicates that there are six sample holders and consequently six circulating pumps this number can easily be extended without requiring excessive costs or space. In such an instance the withdrawing mechanism could be programmed to sample each vial at one minute intervals as well as provided with means and a data station to separate the data from each subsequent piece of data and rapidly provide the operator with a chromatogram or other form of information demonstrating all necessary parameters to describe the dissolution which takes place.

Although the present invention has been described with regard to a particular embodiment, this embodiment is deemed exemplary only and is not limiting. Consequently, the present invention is deemed limited only the appended claims and the reasonable interpretation thereof.

What is claimed is:

1. An apparatus for periodically monitoring the composition of a plurality of samples, said apparatus comprising, in combination:
    a plurality of sample holders each for holding a sample to be tested;
    a plurality of sample flow-through vials, each of said flow-through vials having an inlet and outlet and further including means for enabling the insertion into and withdrawal from each of said flow-through vials of a sample aspirating means;

a plurality of return conduits, each of said return conduits coupling one of said outlets from one of said flow-through vials to one of said sample holders;
  a plurality of sample delivering means each of said delivery means including conveying means for causing fluid from one of said sample holders to be delivered into one of said sample flow-through vials, the fluid being returned to the same holders via a return conduit coupled between said one of said flow-through vials and said one of said holders;
  means, including sample aspirating means, for selectively withdrawing sample fluid from each of said flow-through vials; and
  means for analyzing sample fluid withdrawn by said asperating means whereby said composition of said sample fluid from each of said sample holders is periodically monitored.

2. An apparatus for periodically monitoring the composition of a plurality of samples, said apparatus comprising, in combination:
  a plurality of sample holders each for holding a sample to be tested;
  a plurality of sample flow-through vials, each of said flow through vials having an inlet and outlet and further including means for enabling the insertion into and withdrawal from each of said flow-through vials of a sample aspirating means;
  a plurality of return conduits, each of said return conduits coupling one of said outlets from one of said flow-through vials to one of said sample holders;
  a plurality of sample delivering means each of said delivery means including conveying means for causing fluid from one of said sample holders to be delivered into one of said sample flow-through vials, the fluid being returned to the same holders via a return conduit coupled between said one of said flow-through vials and said one of said holders;
  means, including sample aspirating means, for selectively withdrawing sample fluid from each of said flow-through vials;
  means for analyzing sample fluid withdrawn by said aspirating means whereby said composition of said sample fluid from each of said sample holders is periodically monitored and
  means for controlling said fluid conveying means and said sample fluid withdrawing means whereby said withdrawing means is activated only when fluid is flowing through said one of said sample flow-through vials via said conveying means.

3. An apparatus for periodically monitoring the composition of a plurality of samples, said apparatus comprising, in combination:
  a plurality of sample holders each for holding a sample to be tested;
  a plurality of sample flow-through vials, each of said flow-through vials having an inlet and outlet and further including means for enabling the insertion into and withdrawal from each of said flow-through vials of a sample aspirating means;
  a plurality of return conduits, each of said return conduits coupling one of said outlets from one of said flow-through vials to one of said sample holders;
  a plurality of sample delivering means each of said delivery means including conveying means for causing fluid from one of said sample holders to be delivered into one of said sample flow-through vials, the fluid being returned to the same holders via a return conduit coupled between said one of said flow-through vials and said one of said holders, each of said sample delivery means including a peristaltic pump;
  means, including sample aspirating means, for selectively withdrawing sample fluid from each of said flow-through vials; and
  means for analyzing sample fluid withdrawn by said aspirating means whereby said composition of said sample fluid from each of said sample holders is periodically monitored.

* * * * *